US012369631B2

United States Patent
Mironov et al.

(10) Patent No.: US 12,369,631 B2
(45) Date of Patent: *Jul. 29, 2025

(54) AEROSOL-GENERATING SYSTEM HAVING A FLUID-PERMEABLE HEATER ASSEMBLY

(71) Applicant: Philip Morris Products S.A., Neuchatel (CH)

(72) Inventors: Oleg Mironov, Neuchatel (CH); Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/643,783

(22) Filed: Apr. 23, 2024

(65) Prior Publication Data

US 2024/0268461 A1    Aug. 15, 2024

Related U.S. Application Data

(63) Continuation of application No. 16/999,643, filed on Aug. 21, 2020, now Pat. No. 11,998,051, which is a
(Continued)

(30) Foreign Application Priority Data

Feb. 10, 2014    (EP) .................................... 14154554

(51) Int. Cl.
*A24F 40/46*    (2020.01)
*A24F 40/40*    (2020.01)
(Continued)

(52) U.S. Cl.
CPC .............. *A24F 40/42* (2020.01); *A24F 40/40* (2020.01); *A24F 40/46* (2020.01); *A24F 40/70* (2020.01);
(Continued)

(58) Field of Classification Search
CPC .......................... A61M 11/042; A61M 15/06; A61M 15/0021; A61M 15/0043;
(Continued)

(56) References Cited

U.S. PATENT DOCUMENTS 3,200,819 A    8/1965    Gilbert
3,289,949 A    12/1966    Roth
(Continued)

FOREIGN PATENT DOCUMENTS

CA    2 824 970 A1    8/2012
CN    100593982 C    3/2010
(Continued)

OTHER PUBLICATIONS

Extended European Search Report issued Sep. 3, 2019 in European Patent Application No. 19174753.4, 11 pages.
(Continued)

*Primary Examiner* — Eric S Stapleton
(74) *Attorney, Agent, or Firm* — Oblon, McClelland, Maier & Neustadt, L.L.P.

(57) ABSTRACT

An aerosol-generating system is provided, including a main component and a cartridge that is removably coupled to the main component, the cartridge including a liquid storage portion containing a liquid aerosol-forming substrate and a fluid-permeable electric heater assembly, and the main component includes a power supply, the heater assembly including: an electrically insulating substrate, an aperture being formed in the substrate, and a heater element fixed to the substrate, the heater element spanning the aperture and including a plurality of electrically conductive filaments connected to first and second electrically conductive contact portions, the first and the second contact portions being disposed on opposite sides of the aperture to one another, the first and the second contact portions being configured to
(Continued)

allow contact with the power supply, and the heater assembly being provided at an end of the cartridge that is opposite to a mouthpiece portion of the system.

16 Claims, 15 Drawing Sheets

Related U.S. Application Data continuation of application No. 15/116,652, filed as application No. PCT/EP2014/077835 on Dec. 15, 2014, now Pat. No. 10,842,192.

(51) Int. Cl.

| | |
|---|---|
| A24F 40/42 | (2020.01) |
| A24F 40/70 | (2020.01) |
| A61M 11/04 | (2006.01) |
| A61M 15/06 | (2006.01) |
| H05B 3/06 | (2006.01) |
| H05B 3/14 | (2006.01) |
| H05B 3/16 | (2006.01) |
| H05B 3/34 | (2006.01) |
| A24F 40/10 | (2020.01) |
| A61M 15/00 | (2006.01) |
| A61M 16/00 | (2006.01) |

(52) U.S. Cl.
CPC .......... *A61M 11/042* (2014.02); *A61M 15/06* (2013.01); *H05B 3/06* (2013.01); *H05B 3/145* (2013.01); *H05B 3/16* (2013.01); *H05B 3/34* (2013.01); *H05B 3/342* (2013.01); *H05B 3/347* (2013.01); *A24F 40/10* (2020.01); *A61M 15/0021* (2014.02); *A61M 15/0043* (2014.02); *A61M 2016/0024* (2013.01); *A61M 2205/3653* (2013.01); *A61M 2205/8206* (2013.01); *H05B 2203/011* (2013.01); *H05B 2203/014* (2013.01); *H05B 2203/015* (2013.01); *H05B 2203/017* (2013.01); *H05B 2203/021* (2013.01); *H05B 2203/022* (2013.01)

(58) Field of Classification Search
CPC .. A61M 2205/8206; A61M 2205/3653; A61M 2016/0024; H05B 3/347; H05B 3/342; H05B 3/145; H05B 3/16; H05B 3/06; H05B 3/34; H05B 2203/011; H05B 2203/015; H05B 2203/014; H05B 2203/017; H05B 2203/022; H05B 2203/021; A24F 40/46; A24F 40/40; A24F 40/70; A24F 40/42; A24F 40/10
USPC ........................................................ 392/404
See application file for complete search history.

(56) References Cited

U.S. PATENT DOCUMENTS

| | | | |
|---|---|---|---|
| 3,730,437 A | 5/1973 | Rousselot | |
| 4,273,142 A | 6/1981 | Swanson | |
| 4,462,397 A | 7/1984 | Suzuki | |
| 4,594,969 A | 6/1986 | Przybylski | |
| 4,805,609 A | 2/1989 | Roberts | |
| 4,922,901 A | 5/1990 | Brooks et al. | |
| 4,947,874 A | 8/1990 | Brooks et al. | |
| 4,947,875 A | 8/1990 | Brooks et al. | |
| 4,972,855 A | 11/1990 | Kuriyama | |
| 4,993,436 A | 2/1991 | Bloom, Jr. | |
| 5,137,034 A | 8/1992 | Perfetti | |
| 5,408,574 A * | 4/1995 | Deevi | A24F 40/46 |
| | | | 392/404 |
| 5,490,630 A | 2/1996 | Hecker | |
| 5,530,225 A * | 6/1996 | Hajaligol | A24F 40/46 |
| | | | 131/194 |
| 5,587,207 A * | 12/1996 | Gorokhovsky | H01J 37/32055 |
| | | | 118/721 |
| 5,649,554 A * | 7/1997 | Sprinkel | A24F 40/465 |
| | | | 131/194 |
| 5,827,438 A * | 10/1998 | Blomberg | G01J 3/108 |
| | | | 392/407 |
| 6,357,671 B1 | 3/2002 | Cewers | |
| 6,709,524 B2 | 3/2004 | Kawashima | |
| 7,980,863 B1* | 7/2011 | Holec | H05K 3/363 |
| | | | 439/67 |
| 8,007,286 B1* | 8/2011 | Holec | H05K 1/14 |
| | | | 439/65 |
| 8,146,587 B2 | 4/2012 | Flickinger | |
| 8,162,921 B2 | 4/2012 | Flickinger | |
| 8,499,766 B1 | 8/2013 | Newton | |
| 8,545,463 B2 | 10/2013 | Collins, Jr. | |
| 9,440,020 B2 | 9/2016 | Flickinger | |
| 9,623,205 B2 | 4/2017 | Buchberger | |
| 10,015,990 B2* | 7/2018 | Mironov | H05B 3/146 |
| 10,842,192 B2* | 11/2020 | Mironov | H05B 3/145 |
| 11,998,051 B2* | 6/2024 | Mironov | H05B 3/34 |
| 12,090,269 B2* | 9/2024 | Mironov | B32B 27/12 |
| 2002/0009540 A1 | 1/2002 | Sasaki | |
| 2002/0074329 A1 | 6/2002 | Hayashi | |
| 2003/0015197 A1 | 1/2003 | Hale et al. | |
| 2003/0209534 A1* | 11/2003 | Ferguson | H01C 17/0652 |
| | | | 501/153 |
| 2004/0045956 A1 | 3/2004 | Weiss | |
| 2004/0234916 A1* | 11/2004 | Hale | C06B 33/00 |
| | | | 431/6 |
| 2005/0172976 A1 | 8/2005 | Newman | |
| 2005/0258159 A1* | 11/2005 | Hale | F23Q 3/006 |
| | | | 219/270 |
| 2005/0268911 A1 | 12/2005 | Cross et al. | |
| 2006/0191548 A1 | 8/2006 | Strickland | |
| 2007/0107879 A1 | 5/2007 | Radomski et al. | |
| 2007/0186942 A1 | 8/2007 | Strickland | |
| 2007/0186943 A1 | 8/2007 | Strickland | |
| 2007/0186944 A1 | 8/2007 | Strickland | |
| 2008/0054099 A1 | 3/2008 | Giroux | |
| 2008/0128145 A1 | 6/2008 | Butz | |
| 2008/0276947 A1 | 11/2008 | Martzel | |
| 2009/0014437 A1 | 1/2009 | Van Vooren | |
| 2009/0184107 A1 | 7/2009 | Weiss | |
| 2009/0192443 A1 | 7/2009 | Collins, Jr. | |
| 2009/0212133 A1 | 8/2009 | Collins, Jr. | |
| 2009/0230117 A1 | 9/2009 | Fernando | |
| 2009/0272379 A1* | 11/2009 | Thorens | A61M 15/06 |
| | | | 219/535 |
| 2009/0320863 A1 | 12/2009 | Fernando | |
| 2010/0242974 A1 | 9/2010 | Pan | |
| 2010/0243097 A1 | 9/2010 | Jani | |
| 2011/0036365 A1 | 2/2011 | Chong | |
| 2011/0126848 A1* | 6/2011 | Zuber | A24F 40/46 |
| | | | 131/329 |
| 2011/0226236 A1* | 9/2011 | Buchberger | A61K 31/465 |
| | | | 128/200.23 |
| 2011/0253798 A1* | 10/2011 | Tucker | B05B 1/24 |
| | | | 239/13 |
| 2011/0309157 A1* | 12/2011 | Yang | A61L 9/037 |
| | | | 239/6 |
| 2012/0167906 A1 | 7/2012 | Gysland | |
| 2013/0087160 A1 | 4/2013 | Gherghe | |
| 2013/0139813 A1 | 6/2013 | Storz | |
| 2013/0160764 A1 | 6/2013 | Liu | |
| 2013/0213419 A1 | 8/2013 | Tucker et al. | |
| 2013/0228191 A1 | 9/2013 | Newton | |
| 2014/0008351 A1 | 1/2014 | Verstraeten | |
| 2014/0020693 A1* | 1/2014 | Cochand | A61M 11/041 |
| | | | 131/273 |
| 2014/0202454 A1 | 7/2014 | Buchberger | |
| 2015/0038041 A1 | 2/2015 | Zhamu | |
| 2015/0136156 A1 | 5/2015 | Liu | |

(56) References Cited

U.S. PATENT DOCUMENTS

| | | | |
|---|---|---|---|
| 2015/0190279 A1 | 7/2015 | Acharya et al. | |
| 2024/0268461 A1* | 8/2024 | Mironov | H05B 3/16 |

FOREIGN PATENT DOCUMENTS

| | | |
|---|---|---|
| CN | 102014677 A | 4/2011 |
| CN | 102264420 A | 11/2011 |
| CN | 102551217 A | 7/2012 |
| CN | 102573968 A | 7/2012 |
| CN | 102595943 A | 7/2012 |
| CN | 102861694 A | 1/2013 |
| CN | 103237470 A | 8/2013 |
| CN | 103338664 A | 10/2013 |
| CN | 103533684 A | 1/2014 |
| CN | 103932401 A | 7/2014 |
| CN | 203986096 U | 12/2014 |
| DE | 20 2013100 606 U1 | 4/2013 |
| EA | 2001 00532 A1 | 10/2011 |
| EP | 0 358 002 A2 | 3/1990 |
| EP | 0 822 760 B1 | 6/2003 |
| EP | 2 574 247 A1 | 4/2013 |
| EP | 2 471 392 B1 | 9/2013 |
| JP | 2-124082 A | 5/1990 |
| JP | 6-315366 A | 11/1994 |
| JP | 2002-272830 A | 9/2002 |
| JP | 5008207 B2 | 8/2012 |
| JP | 2014-501107 A | 1/2014 |
| JP | 2017-506076 A | 3/2017 |
| JP | 6438967 B2 | 12/2018 |
| KR | 10-2004-0050925 A | 6/2004 |
| KR | 10-1039837 B1 | 6/2011 |
| KZ | 28018 B | 3/2018 |
| RU | 2 132 629 C1 | 7/1999 |
| RU | 2 389 419 C2 | 2/2010 |
| TW | 201317014 A1 | 5/2013 |
| WO | WO 2006/124757 A2 | 11/2006 |
| WO | WO 2007/077167 A1 | 7/2007 |
| WO | WO 2009/132793 A1 | 11/2009 |
| WO | WO 2010/045671 A1 | 4/2010 |
| WO | WO 2013/013808 A | 1/2013 |
| WO | WO 2013/045582 A2 | 4/2013 |
| WO | WO 2013/083631 A1 | 6/2013 |
| WO | WO 2013/083634 A1 | 6/2013 |
| WO | WO 2013/083635 A1 | 6/2013 |
| WO | WO 2013/126777 A2 | 8/2013 |
| WO | WO 2013/148810 A1 | 10/2013 |
| WO | WO 2013/151295 A1 | 10/2013 |
| WO | WO 2014/012894 A1 | 1/2014 |
| WO | WO 2014/079024 A1 | 5/2014 |
| WO | WO 2015/117704 A1 | 8/2015 |

OTHER PUBLICATIONS

Japanese Office Action issued Nov. 18, 2019 in Japanese Patent Application No. 2018-216569 (with English translation), 6 pages.
Indian Office Action and Search Report issued on Aug. 23, 2019, in Patent Application No. 201617023514, 5 pages.
Combined Chinese Office Action and Search Report issued Chinese Patent Application No. 201480074307.4 (with English translation), 9 pages.
Decision to Grant a Patent issued Oct. 18, 2018 in corresponding Japanese Patent Application No. 2016-551281, 3 pages.
Combined Taiwanese Office Action and Search Report issued Jun. 28, 2018 in Patent Application No. 104104219 (submitting English translation only).
Combined Chinese Office Action and Search Report issued Jun. 28, 2018 in Patent Application No. 201480074307.4 (submitting English translation only).
Decision to Grant issued Nov. 13, 2017 in Kazakhstan Patent Application No. 2016/0755.1 (submitting English translation only), 4 pages.
Decision to Grant issued Mar. 30, 2018 in Russian Patent Application No. 2016136340 (submitting English translation only), 5 pages.
Office Action issued Jul. 11, 2017 in Singaporean Patent Application No. 11201605856U.
International Preliminary Report on Patentability and Written Opinion issued on Aug. 16, 2016 in PCT/EP2014/077835.
International Search Report issued Mar. 25, 2015 in PCT/EP2014/077835 filed Dec. 15, 2014.
Extended European Search Report issued Jan. 26, 2021 in European Patent Application No. 20201274.6, 11 pages.
Japanese Office Action issued Apr. 15, 2021 in Japanese Patent Application No. 2020-104215 (with English translation), 8 pages.
Combined Chinese Office Action and Search Report issued May 20, 2021 in Patent Application No. 201910709330.0 (with English language translation), 13 pages.
Korean Office Action issued Jul. 16, 2021 in Korean Patent Application No. 10-2016-7021288 (with English language translation), 13 pages.
Mesh and Microns Conversion Chart and Information E-book from ISM (Mar. 2020), Industrial Specialties Mfg. and IS MED Specialties, 7 pages.
T 1064/15 3.2.02, Datasheet for the decision of Apr. 23, 2018, 19 pages.
Combined Chinese Office Action and Search Report issued Aug. 3, 2021 in corresponding Chinese Patent Application No. 201910709368.8 (with English Translation), 11 pages.
Combined Russian Office Action and Search Report issued Sep. 27, 2021 in corresponding Russian Patent Application No. 2018119508 (with English Translation), 9 pages.
"Kynol Activated Carbon Fibers & Textiles", Kynol® Information Sheet, 3 pages.
Notice of Allowance issued Jan. 14, 2022 in Korean Patent Application No. 10-2016-7021288 (with English translation), 3 pages.
Combined Chinese Office Action and Search Report issued Jan. 5, 2022 in Patent Application No. 201910709330.0 (with English language translation), 11 pages.
Combined Chinese Notice of Allowance and Search Report with Notification of Patent Registration issued May 27, 2022, in corresponding Chinese Patent Application No. 201910709330.0 (with English Translation and English Translation of Category of Cited Documents), 6 pages.
Japanese Office Action issued on Nov. 16, 2022 in the Japanese Patent Application No. 2021-202171 with English Translation, 3 pages.
Korean Office Action issued Jan. 17, 2023 in Korean Patent Application No. 10-2022-7011581 (with English Translation), 5 pages.
Opponent Post Oral Proceedings mailed Aug. 17, 2023 in corresponding European Application No. 19174753.

* cited by examiner

AEROSOL-GENERATING SYSTEM HAVING A FLUID-PERMEABLE HEATER ASSEMBLY

CROSS-REFERENCE TO RELATED APPLICATIONS

This application is a continuation of and claims benefit under 35 U.S.C. § 120 to U.S. application Ser. No. 16/999,643, filed Aug. 21, 2020, which is a continuation of and claims benefit under 35 U.S.C. § 120 to U.S. application Ser. No. 15/116,652, filed Aug. 4, 2016 (now U.S. Pat. No. 10,842,192), which is a U.S. national stage application of PCT/EP2014/077835, filed on Dec. 15, 2014, and claims the benefit of priority under 35 U.S.C. § 119 from European Patent Application No. 14154554.1, filed on Feb. 10, 2014, the entire contents of each of which are incorporated herein by reference.

TECHNICAL FIELD

The present invention relates to aerosol-generating systems that comprise a heater assembly that is suitable for vapourising a liquid. In particular, the invention relates to handheld aerosol-generating systems, such as electrically operated smoking systems.

DESCRIPTION OF THE RELATED ART

Electrically operated smoking systems that vapourise a liquid by heating to form an aerosol typically comprise a coil of wire that is wrapped around a capillary material that holds the liquid. Electric current passing through the wire causes resistive heating of the wire which vaporises the liquid in the capillary material. The capillary material is typically held within an airflow path so that air is drawn past the wick and entrains the vapour. The vapour subsequently cools to form an aerosol.

This type of system is effective at producing aerosol but it is challenging to manufacture in a low cost and repeatable way. And the wick and coil assembly, together with associated electrical connections, can be fragile and difficult to handle.

It would be desirable to provide a heater assembly suitable for an aerosol-generating system, such as a handheld electrically operated smoking system, that is inexpensive to produce and is robust. It would be further desirable to provide a heater assembly that is more efficient than prior heater assemblies in aerosol-generating systems.

SUMMARY

In one aspect there is provided an aerosol-generating system comprising a fluid-permeable electric heater assembly, the heater assembly comprising: an electrically insulating substrate, an aperture being formed in the electrically insulating substrate; and a heater element fixed to the electrically insulating substrate, the heater element spanning the aperture and comprising a plurality of electrically conductive filaments connected to first and second electrically conductive contact portions, the first and second electrically conductive contact portions positioned on opposite sides of the aperture to one another, wherein the first and second electrically conductive contact portions are configured to allow contact with an external power supply.

BRIEF DESCRIPTION OF THE DRAWINGS

Embodiments of the invention will now be described, by way of example only, with reference to the accompanying drawings, in which.

DETAILED DESCRIPTION

Figure 1A:
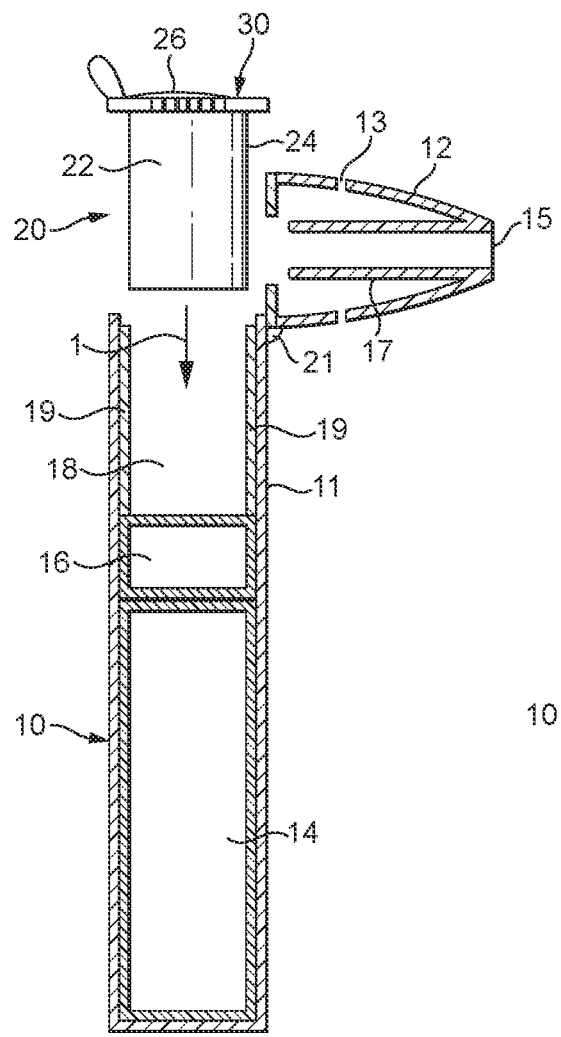
FIGS. 1a to 1d are schematic illustrations of a system, incorporating a cartridge, in accordance with an embodiment of the invention.

The plurality of electrically conductive filaments may form a mesh or array of filaments or may comprise a woven or non-woven fabric.

Advantageously, the heater element has a first face that is fixed to the electrically insulating substrate and the first and second electrically conductive contact portions are configured to allow contact with an external power supply on a second face of the heater element opposite to the first face.

The system may further comprise a liquid storage portion comprising a housing containing a liquid aerosol-forming substrate, wherein the heater assembly is fixed to the housing of the liquid storage portion. The housing is preferably a rigid housing and impermeable to fluid. As used herein "rigid housing" means a housing that is self-supporting. The rigid housing of the liquid storage portion preferably provides mechanical support to the heater assembly.

The liquid storage portion may comprise a capillary material configured to convey liquid aerosol-forming substrate to the heater assembly.

The provision of a heater assembly of this type in an aerosol-generating system has several advantages over a conventional wick and coil arrangement. A heater element comprising a mesh or array of filaments allows for a greater area of the heater to be in contact with a liquid being vapourised. The heater assembly can be inexpensively produced, using readily available materials and using mass production techniques. The heater assembly is robust allowing it to be handled and fixed to other parts of the aerosol-generating system during manufacture, and in particular to form part of a removable cartridge. The provision of electrically conductive contact portions forming part of the heater element allows for reliable and simple connection of the heater assembly to a power supply.

The electrically conductive filaments may be substantially flat. As used herein, "substantially flat" means formed in a single plane and not wrapped around or other conformed to fit a curved or other non-planar shape. A flat heater assembly can be easily handled during manufacture and provides for a robust construction.

The electrically conductive filaments may define interstices between the filaments and the interstices may have a width of between 10 µm and 100 µm. Preferably the filaments give rise to capillary action in the interstices, so that in use, liquid to be vapourised is drawn into the interstices, increasing the contact area between the heater assembly and the liquid.

The electrically conductive filaments may form a mesh of size between 160 and 600 Mesh US (+/−10%) (i.e., between 160 and 600 filaments per inch (+/−10%)). The width of the interstices is preferably between 75 µm and 25 µm. The percentage of open area of the mesh, which is the ration of the area of the interstices to the total area of the mesh is preferably between 25 and 56%. The mesh may be formed using different types of weave or lattice structures. Alternatively, the electrically conductive filaments consist of an array of filaments arranged parallel to one another.

The mesh, array or fabric of electrically conductive filaments may also be characterised by its ability to retain liquid, as is well understood in the art.

The electrically conductive filaments may have a diameter of between 8 µm and 100 µm, preferably between 8 µm and 50 µm, and more preferably between 8 µm and 39 µm.

The area of the mesh, array or fabric of electrically conductive filaments may be small, preferably less than or equal to 25 $mm^2$, allowing it to be incorporated in to a handheld system. The mesh, array or fabric of electrically conductive filaments may, for example, be rectangular and have dimensions of 5 mm by 2 mm. Preferably, the mesh or array of electrically conductive filaments covers an area of between 10% and 50% of the area of the heater assembly. More preferably, the mesh or array of electrically conductive filaments covers an area of between 15 and 25% of the area of the heater assembly.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, TIMETAL®, iron-aluminium based alloys and iron-manganese-aluminium based alloys. TIMETAL® is a registered trademark of Titanium Metals Corporation. The filaments may be coated with one or more insulators. Preferred materials for the electrically conductive filaments are 304, 316, 304L, and 316L stainless steel, and graphite.

The electrical resistance of the mesh, array, or fabric of electrically conductive filaments of the heater element is preferably between 0.3 and 4 Ohms. More preferably, the electrical resistance of the mesh, array or fabric of electrically conductive filaments is between 0.5 and 3 Ohms, and more preferably about 1 Ohm. The electrical resistance of the mesh, array or fabric of electrically conductive filaments is preferably at least an order of magnitude, and more preferably at least two orders of magnitude, greater than the electrical resistance of the contact portions. This ensures that the heat generated by passing current through the heater element is localised to the mesh or array of electrically conductive filaments. It is advantageous to have a low overall resistance for the heater element if the system is powered by a battery. Minimizing parasitic losses between the electrical contacts and the mesh or the filaments is also desirable to minimize parasitic power losses. A low resistance, high current system allows for the delivery of high power to the heater element. This allows the heater element to heat the electrically conductive filaments to a desired temperature quickly.

The first and second electrically conductive contact portions may be fixed directly to the electrically conductive filaments. The contact portions may be positioned between the electrically conductive filaments and the electrically insulating substrate. For example, the contact portions may be formed from a copper foil that is plated onto the insulating substrate. The contact portions may also bond more readily with the filaments than the insulating substrate would.

Alternatively, the first and second electrically conductive contact portions may be integral with the electrically conductive filaments. For example, the heater element may be formed by etching a conductive sheet to provide a plurality of filaments between two contact portions.

The heater assembly may comprise at least one filament made from a first material and at least one filament made from a second material different from the first material. This may be beneficial for electrical or mechanical reasons. For example, one or more of the filaments may be formed from a material having a resistance that varies significantly with temperature, such as an iron aluminium alloy. This allows a measure of resistance of the filaments to be used to determine temperature or changes in temperature. This can be used in a puff detection system and for controlling heater temperature to keep it within a desired temperature range.

The electrically insulating substrate may comprise any suitable material, and is preferably a material that is able to tolerate high temperatures (in excess of 300° C.) and rapid temperature changes. An example of a suitable material is a polyimide film, such as Kapton®.

The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-containing material containing volatile tobacco flavour compounds, which are released from the aerosol-forming substrate upon heating. The aerosol-forming substrate may alternatively comprise a non-tobacco-containing material. The aerosol-forming substrate may comprise homogenised plant-based material. The aerosol-forming substrate may comprise homogenised tobacco material. The aerosol-forming substrate may comprise at least one aerosol-former. An aerosol-former is any suitable known compound or mixture of compounds that, in use, facilitates formation of a dense and stable aerosol and that is substantially resistant to thermal degradation at the operating temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and, most preferred, glycerine. The aerosol-forming substrate may comprise other additives and ingredients, such as flavourants.

The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid to the heater. Alternatively, the capillary material may comprise sponge-like or foam-like material. The structure of the capillary material forms a plurality of small bores or tubes, through which the liquid can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid has physical properties, including but not limited to viscosity, surface tension, density, thermal conductivity, boiling point, and vapour pressure, which allow the liquid to be transported through the capillary device by capillary action.

The capillary material may be in contact with the electrically conductive filaments. The capillary material may extend into interstices between the filaments. The heater assembly may draw liquid aerosol-forming substrate into the interstices by capillary action. The capillary material may be in contact with the electrically conductive filaments over substantially the entire extent of the aperture.

The housing may contain two or more different capillary materials, wherein a first capillary material, in contact with the heater element, has a higher thermal decomposition temperature and a second capillary material, in contact with the first capillary material but not in contact with the heater element has a lower thermal decomposition temperature. The first capillary material effectively acts as a spacer separating the heater element from the second capillary material so that the second capillary material is not exposed to temperatures above its thermal decomposition temperature. As used herein, "thermal decomposition temperature" means the temperature at which a material begins to decompose and lose mass by generation of gaseous by products.

The second capillary material may advantageously occupy a greater volume than the first capillary material and may hold more aerosol-forming substrate that the first capillary material. The second capillary material may have superior wicking performance to the first capillary material. The second capillary material may be a less expensive or have a higher filling capability than the first capillary material. The second capillary material may be polypropylene.

The first capillary material may separate the heater assembly from the second capillary material by a distance of at least 1.5 mm, and preferably between 1.5 and 2 mm in order to provide a sufficient temperature drop across the first capillary material.

The liquid storage portion may be positioned on a first side of the electrically conductive filaments and an airflow channel positioned on an opposite side of the electrically conductive filaments to the liquid storage portion, such that air flow past the electrically conductive filaments entrains vapourised liquid aerosol-forming substrate.

The system may further comprise electric circuitry connected to the heater element and to an electrical power source, the electric circuitry configured to monitor the electrical resistance of the heater element or of one or more filaments of the heater element, and to control the supply of power to the heater element from the power source dependent on the electrical resistance of the heater element or specifically the electrical resistance of the one or more filaments.

The electric circuitry may comprise a microprocessor, which may be a programmable microprocessor, a microcontroller, or an application specific integrated chip (ASIC) or other electronic circuitry capable of providing control. The electric circuitry may comprise further electronic components. The electric circuitry may be configured to regulate a supply of power to the heater. Power may be supplied to the heater element continuously following activation of the system or may be supplied intermittently, such as on a puff-by-puff basis. The power may be supplied to the heater element in the form of pulses of electrical current.

The system advantageously comprises a power supply, typically a battery such as a lithium iron phosphate battery, within the main body of the housing. As an alternative, the power supply may be another form of charge storage device such as a capacitor. The power supply may require recharging and may have a capacity that allows for the storage of enough energy for one or more smoking experiences. For example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations of the heater.

The system may comprise a main unit and a cartridge that is removably coupled to the main unit, wherein the liquid storage portion and heater assembly are provided in the cartridge and the main unit comprises a power supply. As used herein, the cartridge being "removably coupled" to the device means that the cartridge and device can be coupled and uncoupled from one another without significantly damaging either the device or the cartridge.

The system may be an electrically operated smoking system. The system may be a handheld aerosol-generating system. The aerosol-generating system may have a size comparable to a conventional cigar or cigarette. The smoking system may have a total length between approximately 30 mm and approximately 150 mm. The smoking system may have an external diameter between approximately 5 mm and approximately 30 mm.

In a second aspect, there is provided a fluid-permeable electric heater assembly comprising: an electrically insulating substrate, an aperture being formed in the electrically insulating substrate; and a heater element spanning the aperture and having a first face fixed to the electrically insulating substrate, the heater element comprising a plurality of electrically conductive filaments connected to first and second electrically conductive contact portions, the first and second electrically conductive contact portions positioned on opposite sides of the aperture to one another, wherein the first and second electrically conductive, contact portions are configured to allow contact with an external power supply.

In a third aspect, there is provided a method of manufacturing a fluid-permeable electric heater assembly suitable for use in an aerosol-generating system, comprising:

providing an electrically insulating substrate;
forming one or more apertures in the substrate;
providing a heater element on the substrate spanning the one or more apertures, the heater element comprising a plurality of electrically conductive filaments and at least two electrically conductive contact portions on opposite sides of the one or more apertures to one another.

In a fourth aspect, there is provided a method of manufacturing a plurality of fluid-permeable electric heater assemblies suitable for use in an aerosol-generating system, comprising:

providing an electrically insulating substrate;
forming a plurality of apertures in the substrate;
providing a plurality of electrically conductive contact portions on the substrate on opposite sides of each of the plurality of apertures to one another;
providing a plurality of electrically conductive filaments on the substrate extending between the electrically conductive contact portions across each of the plurality apertures to provide a heater assembly array;
cutting a plurality of individual heater assemblies from the heater assembly array, each heater assembly including one of the apertures.

The electrically insulating substrate may be a flexible sheet material. The electrically conductive contact portions and electrically conductive filaments may be integrally formed with one another.

Features described in relation to one aspect may equally be applied to other aspects of the invention. In particular, features described in relation to the heater assembly in the first aspect of the invention, may equally be applied to the heater assembly of the second aspect of the invention.

As used herein, "electrically conductive" means formed from a material having a resistivity of $1 \times 10^{-4}$ Ωm, or less. As used herein, "electrically insulating" means formed from a material having a resistivity of $1 \times 10^4$ Ωm or more.

FIGS. 1a to 1d are schematic illustrations of an aerosol-generating system, including a cartridge in accordance with an embodiment of the invention. FIG. 1a is a schematic view of an aerosol-generating device 10 and a separate cartridge 20, which together form the aerosol-generating system. In this example, the aerosol-generating system is an electrically operated smoking system.

The cartridge 20 contains an aerosol-forming substrate and is configured to be received in a cavity 18 within the device. Cartridge 20 should be replaceable by a user when the aerosol-forming substrate provided in the cartridge is depleted. FIG. 1a shows the cartridge 20 just prior to insertion into the device, with the arrow 1 in FIG. 1a indicating the direction of insertion of the cartridge.

The aerosol-generating device 10 is portable and has a size comparable to a conventional cigar or cigarette. The device 10 comprises a main body 11 and a mouthpiece portion 12. The main body 11 contains a battery 14, such as a lithium iron phosphate battery, control electronics 16 and a cavity 18. The mouthpiece portion 12 is connected to the main body 11 by a hinged connection 21 and can move between an open position as shown in FIG. 1 and a closed position as shown in FIG. 1d. The mouthpiece portion 12 is placed in the open position to allow for insertion and removal of cartridges 20 and is placed in the closed position when the system is to be used to generate aerosol, as will be described. The mouthpiece portion comprises a plurality of air inlets 13 and an outlet 15. In use, a user sucks or puffs on the outlet to draw air from the air inlets 13, through the mouthpiece portion to the outlet 15, and thereafter into the mouth or lungs of the user. Internal baffles 17 are provided to force the air flowing through the mouthpiece portion 12 past the cartridge, as will be described.

The cavity 18 has a circular cross-section and is sized to receive a housing 24 of the cartridge 20. Electrical connectors 19 are provided at the sides of the cavity 18 to provide an electrical connection between the control electronics 16 and battery 14 and corresponding electrical contacts on the cartridge 20.

Figure 1B:
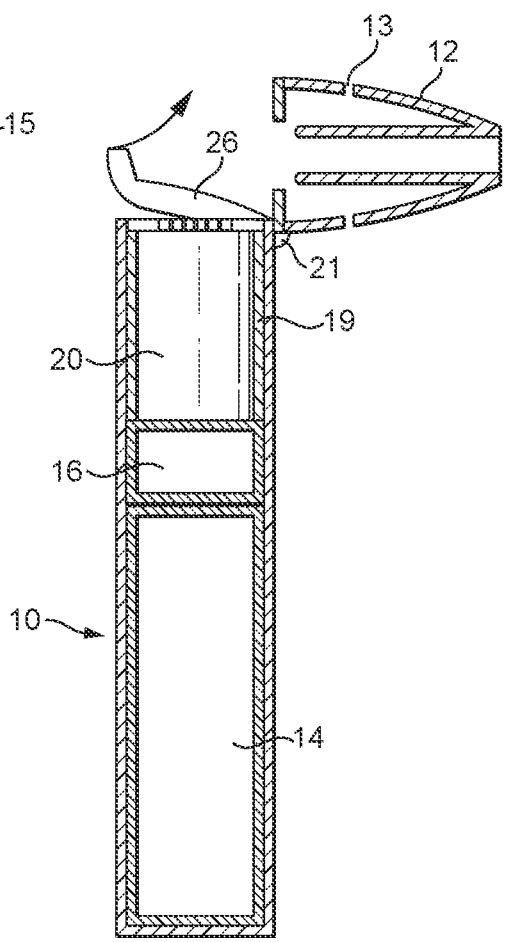

FIG. 1b shows the system of FIG. 1a with the cartridge inserted into the cavity 18, and the cover 26 being removed. In this position, the electrical connectors rest against the electrical contacts on the cartridge, as will be described.

Figure 1C:
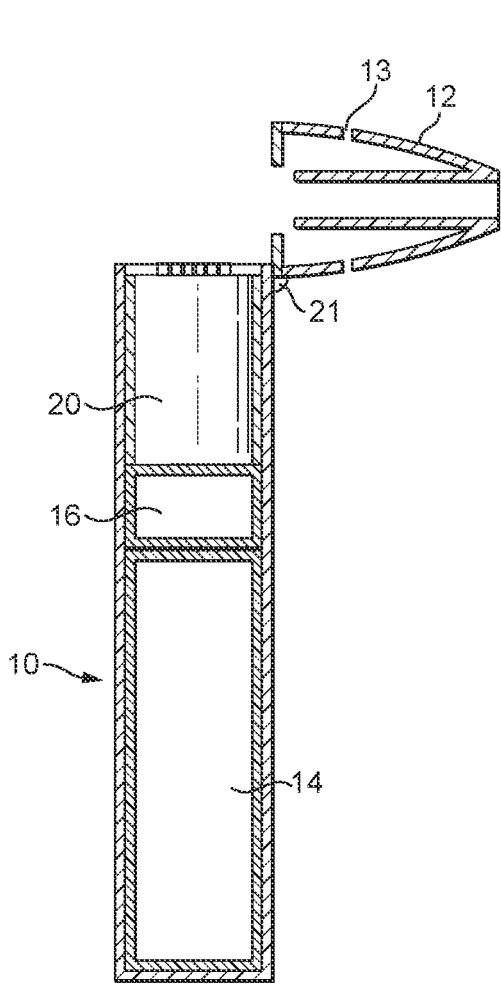
Figure 1D:
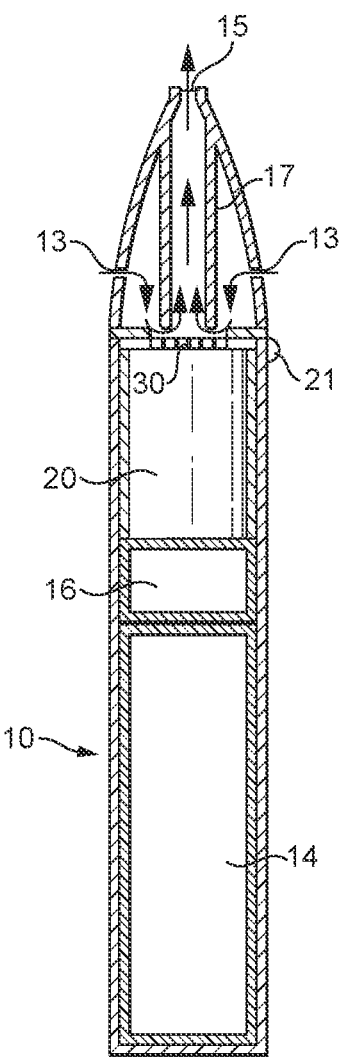

FIG. 1c shows the system of FIG. 1b with the cover 26 fully removed and the mouthpiece portion 12 being moved to a closed position.

Figure 2:
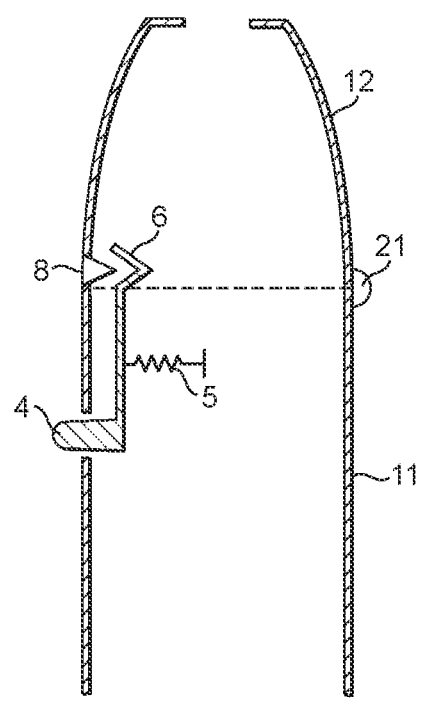
FIG. 2 is a schematic illustration of a clasp mechanism for the mouthpiece portion of the system of FIG. 1.

FIG. 1d shows the system of FIG. 1c with the mouthpiece portion 12 in the closed position. The mouthpiece portion 12 is retained in the closed position by a clasp mechanism, as is schematically illustrated in FIG. 2. FIG. 2 illustrates the main body 11 and mouthpiece portion 12 connected by hinged connection 21. The mouthpiece portion 12 comprises an inwardly extending tooth 8. When the mouthpiece portion is in a closed position, the tooth 8 engages a clasp 6 on the main body of the device. The clasp 6 is biased by biasing spring 5 to engage the tooth 8. A button 4 is fixed to the clasp 6. Button 4 can be depressed by a user against the action of the biasing spring 5 to release the tooth 8 from the clasp 6, allowing the mouthpiece portion to move to an open position. It will now be apparent to a person of ordinary skill in the art that other suitable mechanisms for retaining the mouthpiece in a closed position may be used, such as a snap fitting or a magnetic closure.

The mouthpiece portion 12 in a closed position retains the cartridge in electrical contact with the electrical connectors 19 so that a good electrical connection is maintained in use, whatever the orientation of the system is. The mouthpiece portion 12 may include an annular elastomeric element that engages a surface of the cartridge and is compressed between a rigid mouthpiece housing element and the cartridge when the mouthpiece portion 12 is in the closed position. This ensures that a good electrical connection is maintained despite manufacturing tolerances.

Figure 8:
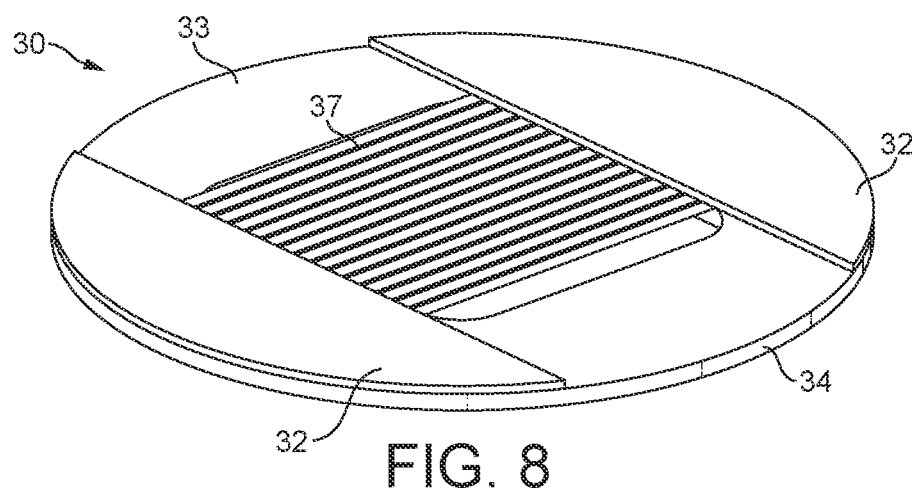
FIG. 8 is a detail view of a further alternative heater assembly that can be used in the cartridge shown in FIG. 2.
Figure 9:
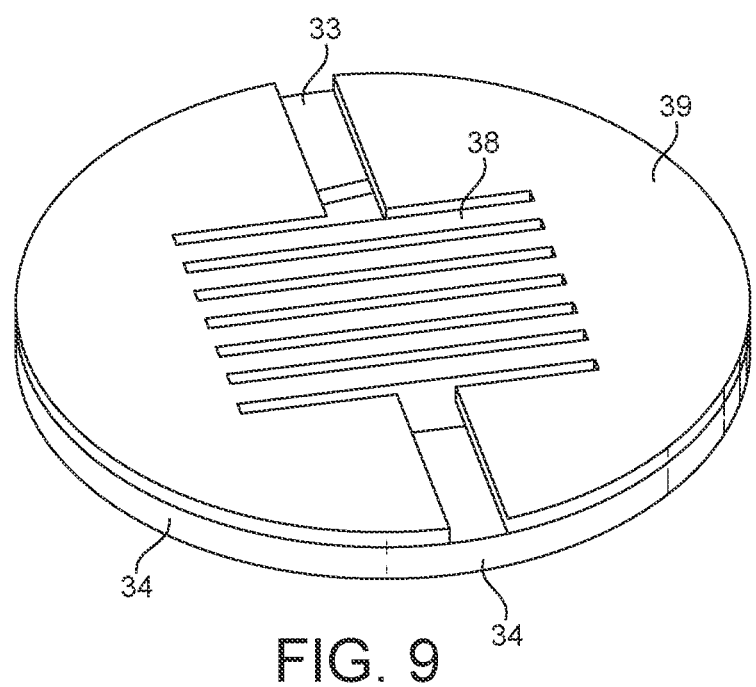
FIG. 9 is a detail view of a still further alternative heater assembly that can be used in the cartridge shown in FIG. 2.
Figure 10:
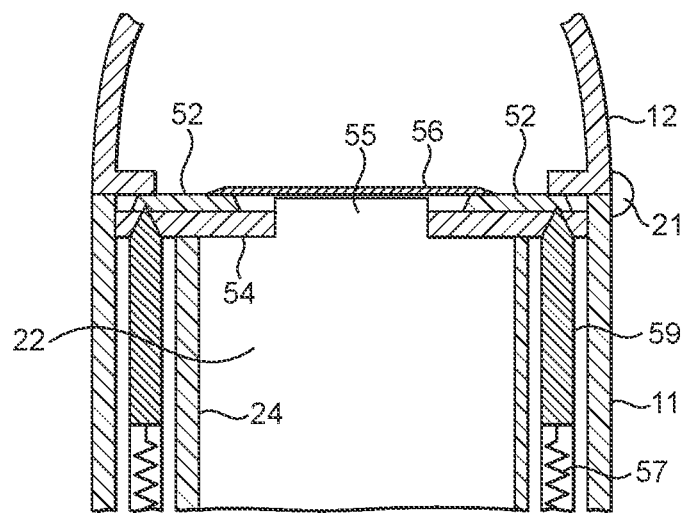
FIG. 10 is a detail view of alternative mechanism for making electrical contact between the device and the heater assembly.
Figure 11A:
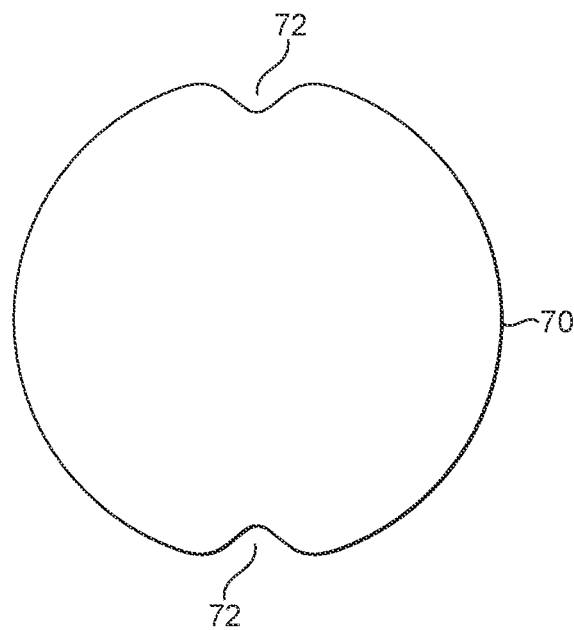
FIGS. 11a and 11b illustrate some cartridge housing shapes that can be used to ensure correct alignment of the cartridge in the device.
Figure 11B:
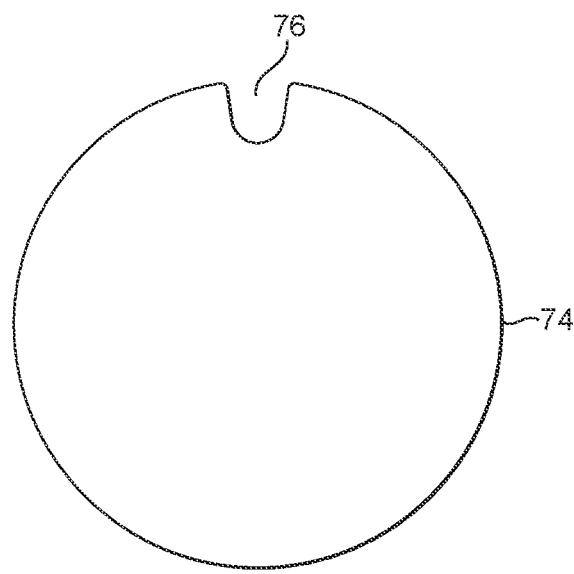

Of course other mechanisms for maintaining a good electrical connection between the cartridge and the device may, alternatively or in addition, be employed. For example, the housing 24 of the cartridge 20 may be provided with a thread or groove (not illustrated) that engages a corresponding groove or thread (not illustrated) formed in the wall of the cavity 18. A threaded engagement between the cartridge and device can be used to ensure the correct rotational alignment as well as retaining the cartridge in the cavity and ensuring a good electrical connection. The threaded connection may extend for only half a turn or less of the cartridge, or may extend for several turns. Alternatively, or in addition, the electrical connectors 19 may be biased into contact with the contacts on the cartridge, as will be described with reference to FIG. 8.

Figure 3:
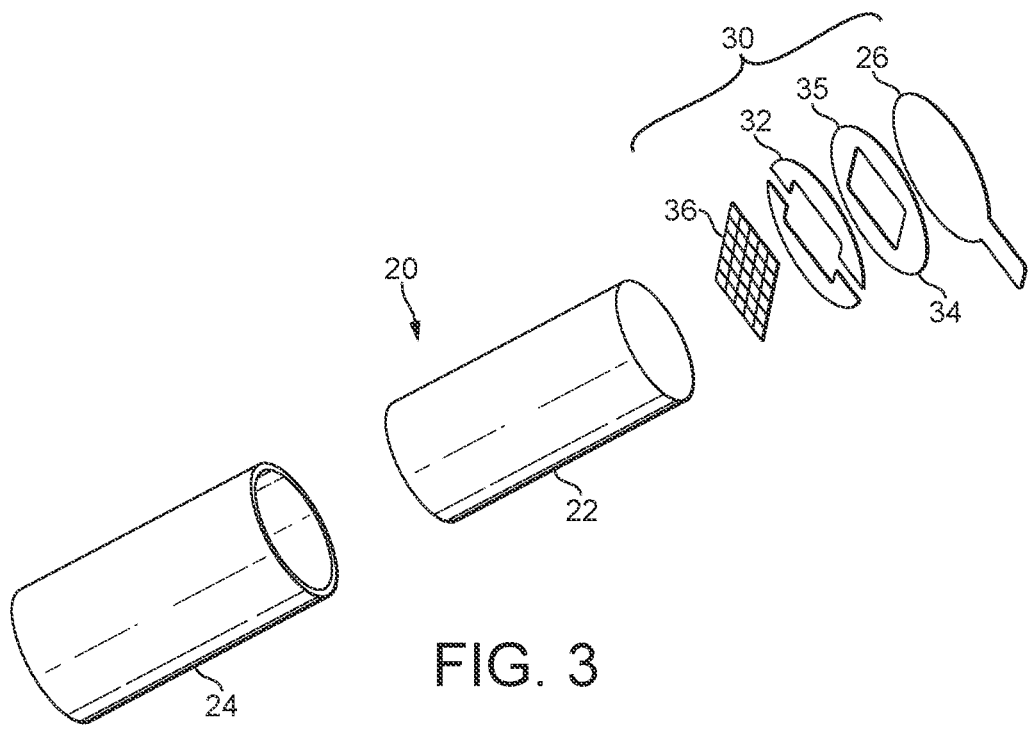
FIG. 3 is an exploded view of the cartridge of FIGS. 1a to 1d.

FIG. 3 is an exploded view of the cartridge 20. The cartridge 20 comprises a generally circular cylindrical housing 24 that has a size and shape selected to be received into the cavity 18. The housing contains a capillary material 22 that is soaked in a liquid aerosol-forming substrate. In this example the aerosol-forming substrate comprises 39% by weight glycerine, 39% by weight propylene glycol, 20% by weight water and flavourings, and 2% by weight nicotine. A capillary material is a material that actively conveys liquid from one end to another, and may be made from any suitable material. In this example the capillary material is formed from polyester.

The housing has an open end to which a heater assembly 30 is fixed. The heater assembly 30 comprises a substrate 34 having an aperture 35 formed in it, a pair of electrical contacts 32 fixed to the substrate and separated from each other by a gap 33, and a plurality of electrically conductive heater filaments 36 spanning the aperture and fixed to the electrical contacts on opposite sides of the aperture 35.

The heater assembly 30 is covered by a removable cover 26. The cover comprises a liquid impermeable plastic sheet that is glued to the heater assembly but which can be easily peeled off. A tab is provided on the side of the cover to allow a user to grasp the cover when peeling it off. It will now be apparent to one of ordinary skill in the art that although gluing is described as the method to a secure the impermeable plastic sheet to the heater assembly, other methods familiar to those in the art may also be used including heat sealing or ultrasonic welding, so long as the cover may easily be removed by a consumer.

Figure 4:
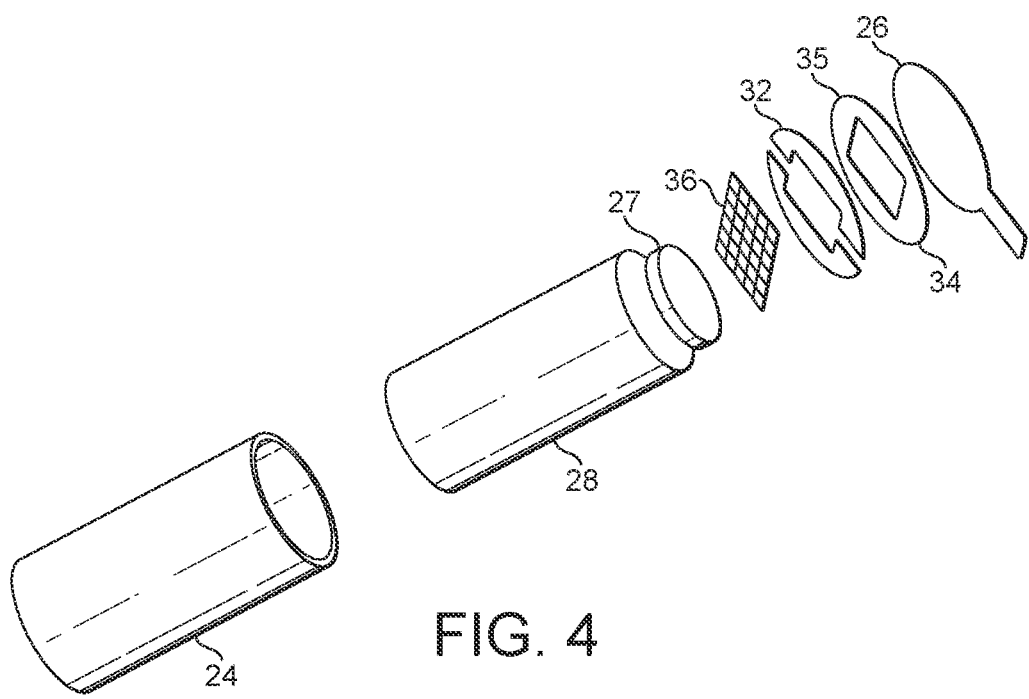
FIG. 4 is an exploded view of an alternative cartridge for use in a system as shown in FIGS. 1a to 1d.

FIG. 4 is an exploded view of an alternative exemplary cartridge. The cartridge of FIG. 4 is the same size and shape as the cartridge of FIG. 3 and has the same housing and heater assembly. However, the capillary material within the cartridge of FIG. 4 is different to that of FIG. 3. There are two separate capillary materials 27, 28 in the cartridge of FIG. 4. A disc of a first capillary material 27 is provided to contact the heater element 36, 32 in use. A larger body of a second capillary material 28 is provided on an opposite side of the first capillary material 27 to the heater assembly. Both the first capillary material and the second capillary material retain liquid aerosol-forming substrate. The first capillary material 27, which contacts the heater element, has a higher thermal decomposition temperature (at least 160° C. or higher such as approximately 250° C.) than the second capillary material 28. The first capillary material 27 effectively acts as a spacer separating the heater element 36, 32 from the second capillary material 28 so that the second capillary material is not exposed to temperatures above its thermal decomposition temperature. The thermal gradient across the first capillary material is such that the second capillary material is exposed to temperatures below its thermal decomposition temperature. The second capillary material 28 may be chosen to have superior wicking performance to the first capillary material 27, may retain more liquid per unit volume than the first capillary material and may be less expensive than the first capillary material. In this example the first capillary material is a heat resistant material, such as a fiberglass or fiberglass containing material and the second capillary material is a polymer such as suitable capillary material. Exemplary suitable capillary materials include the capillary materials discussed herein and in alternative embodiments may include high density polyethylene (HDPE), or polyethylene terephthalate (PET).

Figure 5A:
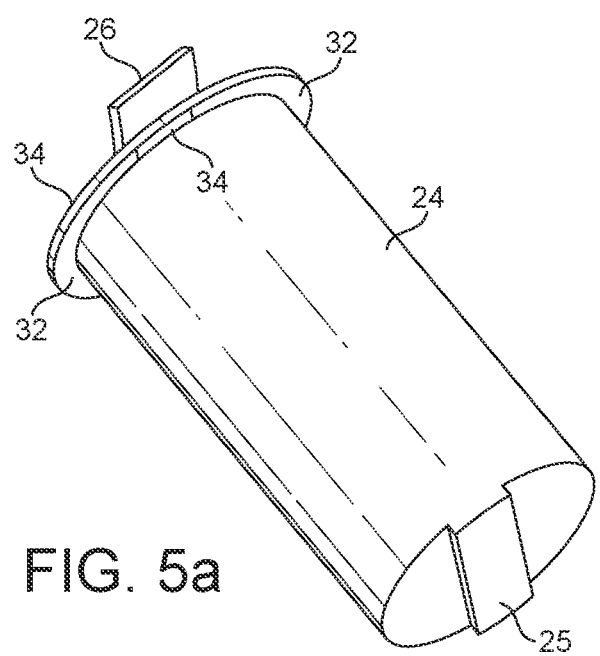
FIG. 5a is a perspective underside view of the cartridge of FIG. 2.

FIG. 5a is a perspective underside view of the cartridge of FIG. 3. It can be seen from FIG. 5a that the heater assembly extends in a lateral plane and extends laterally beyond the housing 24 so that the heater assembly forms a lip around the top of the housing 24. Exposed portions of the electrical contacts 32 face in an insertion direction of the cartridge so that when the cartridge is fully inserted into the cavity 18, the exposed portions of the contacts 32 contact the electrical connectors 19. The tab, provided on the side of the cover 26 to allow a user to grasp the cover when peeling it off, can be clearly seen. FIG. 5a also illustrates a locating portion 25 formed on the base of the cartridge for ensuring the correct orientation of the cartridge in the cavity of the device. The locating portion 25 is part of the injection moulded housing 24 and is configured to be received in a corresponding slot (not illustrated) in the base of the cavity 18. When the locating portion 25 is received in the slot in the cavity, the contacts 32 are aligned with the connectors 19.

Figure 5B:
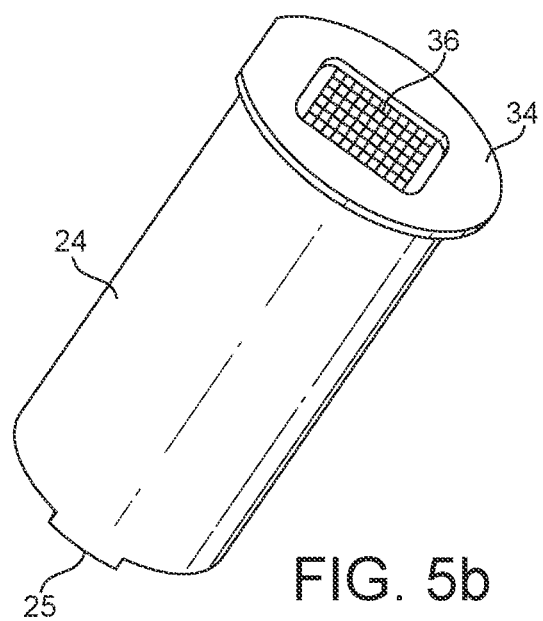
FIG. 5b is a perspective topside view of the cartridge of FIG. 2, with the cover removed.

FIG. 5b is a perspective topside view of the cartridge of FIG. 3, with the cover removed. The heater filaments 36 are exposed through the aperture 35 in the substrate 34 so that vapourised aerosol-forming substrate can escape into the air flow past the heater assembly.

The housing 24 is formed from a thermoplastic, such as polypropylene. The heater assembly 30 is glued to the housing 24 in this example. However, there are several possible ways in which to assembly and fill the cartridge.

Figure 13A:
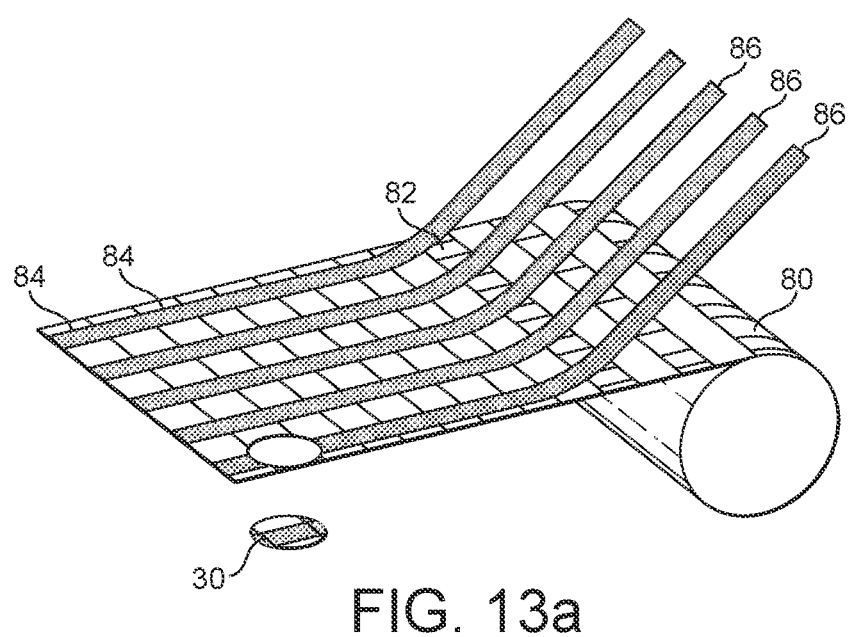
FIGS. 13a, 13b and 13c illustrate alternative methods of manufacture for a heater assembly in accordance with the invention.
Figure 13B:
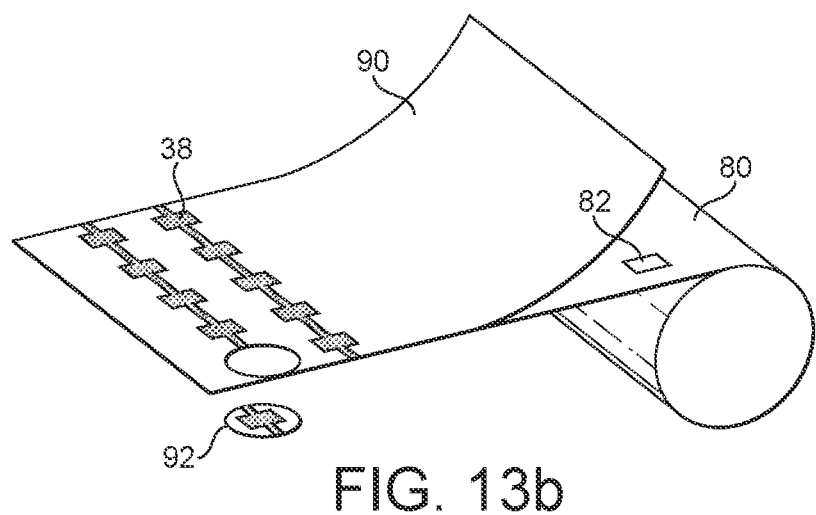
Figure 13C:
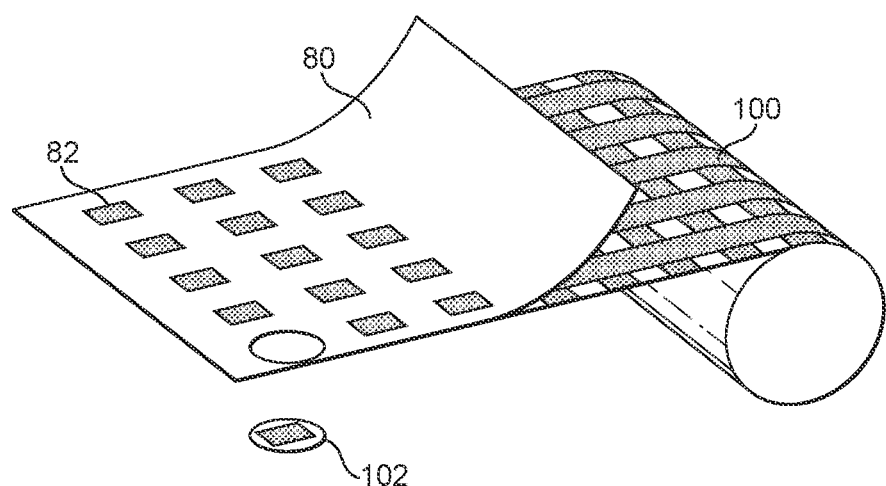

The cartridge housing may be formed by injection moulding. The capillary materials 22, 27, 28 may be formed by cutting suitable lengths of capillary material from a long rod of capillary fibres. The heater assembly may be assembled using a process as described with reference to FIGS. 13a, 13b and 13c. In one embodiment the cartridge is assembled by first inserting the one or more capillary materials 22, 27, 28 into the housing 24. A predetermined volume of liquid aerosol-forming substrate is then introduced into the housing 24, soaking the capillary materials. The heater assembly 30 is then pushed onto the open end of the housing and fixed to the housing 24 by gluing, welding, heat sealing, ultrasonic welding, or other methods that will now be apparent to one of ordinary skill in the art. The temperature of the housing is preferably held below 160° C. during any sealing operation to prevent unwanted volatising of the aerosol-forming substrate. The capillary material may be cut to a length such that it extends out of the open end of the housing 24 until it is compressed by the heater assembly. This promotes transport of aerosol-forming substrate into the interstices of the heater element in use.

In another embodiment, instead of pressing the heater assembly 30 onto the housing 24 and then sealing, the heater assembly and the open end of the housing may first be flash heated and then pressed together to bond the heater assembly 30 to the housing 24.

It is also possible to assemble the heater assembly 30 to the housing 24 before filling the housing with aerosol-forming substrate and subsequently to introduce the aerosol-forming substrate in to the housing 24. In that case, the heater assembly may be fixed to the cartridge using any of the methods described. The heater assembly or housing is then pierced using a hollow needle and the aerosol-forming substrate injected into the capillary material 22, 27, 28. Any opening made by the hollow needle is then sealed by heat sealing or by using a sealing tape.

Figure 6:
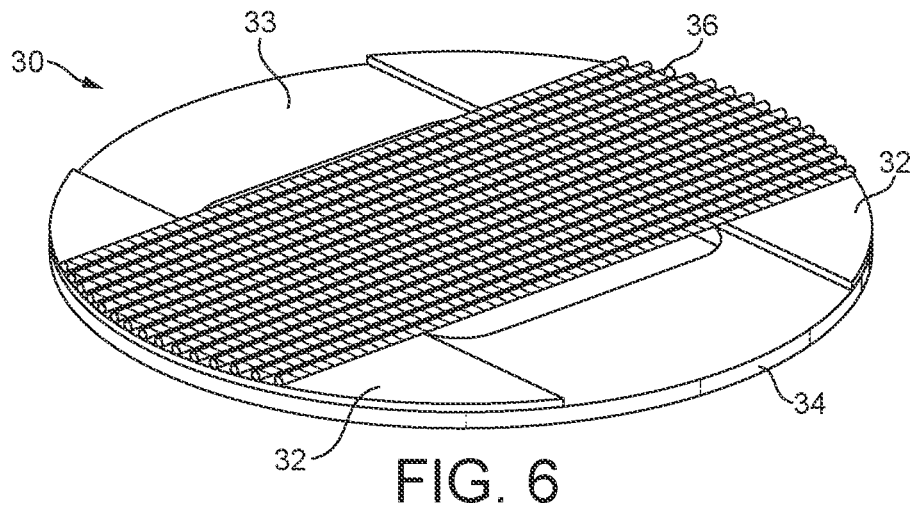
FIG. 6 is a detail view of a heater assembly used in the cartridge shown in FIG. 2.
Figure 7:
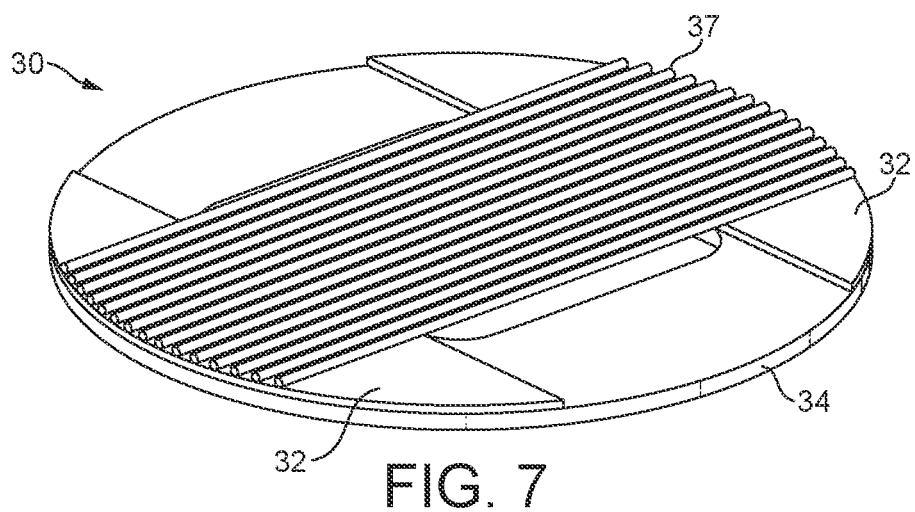
FIG. 7 is a detail view of an alternative heater assembly that can be used in the cartridge shown in FIG. 2.
Figure 12A:
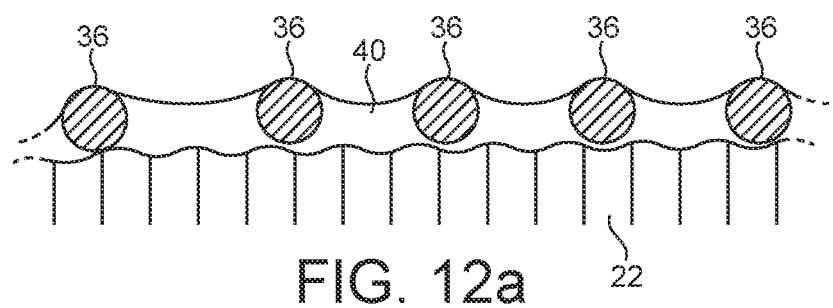
FIG. 12a is a detailed view of the filaments of the heater, showing a meniscus of liquid aerosol-forming substrate between the filaments.
Figure 12B:
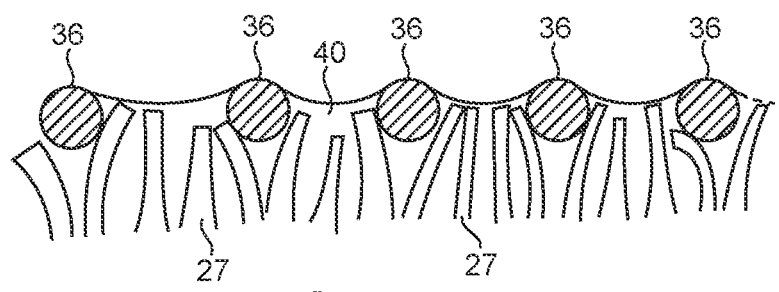
FIG. 12b is a detailed view of the filaments of the heater, showing a meniscus of liquid aerosol-forming substrate between the filaments and a capillary material extending between the filaments.

FIG. 6 is an illustration of a first heater assembly 30 in accordance with the disclosure. The heater assembly comprises a mesh formed from 304L stainless steel, with a mesh size of about 400 Mesh US (about 400 filaments per inch). The filaments have a diameter of around 16 μm. The mesh is connected to electrical contacts 32 that are separated from each other by a gap 33 and are formed from a copper foil having a thickness of around 30 μm. The electrical contacts 32 are provided on a polyimide substrate 34 having a thickness of about 120 μm. The filaments forming the mesh define interstices between the filaments. The interstices in this example have a width of around 37 μm, although larger or smaller interstices may be used. Using a mesh of these approximate dimensions allows a meniscus of aerosol-forming substrate to be formed in the interstices, and for the mesh of the heater assembly to draw aerosol-forming substrate by capillary action. The open area of the mesh, i.e., the ratio of the area of interstices to the total area of the mesh is advantageously between 25 and 56%. The total resistance of the heater assembly is around 1 Ohm. The mesh provides the vast majority of this resistance so that the majority of the heat is produced by the mesh. In this example the mesh has an electrical resistance more than 100 times higher than the electrical contacts 32.

The substrate 34 is electrically insulating and, in this example, is formed from a polyimide sheet having a thickness of about 120 μm. The substrate is circular and has a diameter of 8 mm. The mesh is rectangular and has side lengths of 5 mm and 2 mm. These dimensions allow for a complete system having a size and shape similar to a convention cigarette or cigar to be made. Another example of dimensions that have been found to be effective is a circular substrate of diameter 5 mm and a rectangular mesh of 1 mm×4 mm.

FIG. 7 is an illustration of an alternative, exemplary heater assembly in accordance with the disclosure. The heater assembly of FIG. 7 is the same as that shown in FIG. 6 but the mesh 36 is replaced by an array of parallel electrically conductive filaments 37. The array of filaments 37 are formed from 304L stainless steel and have a diameter of around 16 μm. The substrate 34 and copper contact 32 are as described with reference to FIG. 6.

FIG. 8 is an illustration of another alternative heater assembly in accordance with the disclosure. The heater assembly of FIG. 8 is the same as that shown in FIG. 7 but in the assembly of FIG. 8, the filaments 37 are bonded directly to the substrate 34 and the contacts 32 are then bonded onto the filaments. The contacts 32 are separated from each other by insulating gap 33 as before, and are formed from copper foil of a thickness of around 30 μm. The same arrangement of substrate filaments and contacts can be used for a mesh type heater as shown in FIG. 6. Having the contacts as an outermost layer can be beneficial for providing reliable electrical contact with a power supply.

FIG. 9 is an illustration of an alternative heater assembly in accordance with the disclosure. The heater assembly of FIG. 9 comprises a plurality of heater filaments 38 that are integrally formed with electrical contacts 39. Both the filaments and the electrical contacts are formed from a stainless steel foil that is etched to define filaments 38. The contacts 39 are separated by a gap 33 except when joined by filaments 38. The stainless steel foil is provided on a polyimide substrate 34. Again the filaments 38 provide the vast majority of this resistance, so that the majority of the heat is produced by the filaments. In this example the filaments 38 have an electrical resistance more than 100 times higher than the electrical contacts 39.

In the cartridge shown in FIGS. 3, 4 and 5, the contacts 32 and filaments 36, 38 are located between the substrate layer 34 and the housing 24. However, it is possible to mount the heater assembly to the cartridge housing the other way up, so that the polyimide substrate is directly adjacent to the housing 24. FIG. 10 illustrates an arrangement of this type. FIG. 10 shows a heater assembly comprising a stainless steel mesh 56, fixed to copper foil contacts 52. The copper contacts 52 are fixed to a polyimide substrate 54. An aperture 55 is formed in the polyimide substrate 54. The polyimide substrate is welded to the housing 24 of the cartridge. A capillary material 22, soaked in aerosol-forming substrate, fills the housing and extends through the aperture to contact the mesh 55. The cartridge is shown received in the main body 11 of the device and held between electrical connectors 59 and mouthpiece portion 12. In this embodiment, in order for the electrical connectors 59 to make an electrical connection with the contacts 52, the connectors 59 are adapted to pierce the polyimide substrate 54, as shown. The electrical connectors are made with sharpened ends and are urged into contact with the heater assembly by springs 57. The polyimide substrate may be pre-scored to ensure a good electrical contact is made, or may even be provided with apertures so that piercing of the substrate is not necessary. The springs 57 also ensure that a good electrical contact between the contacts 52 and the connectors 59 is maintained whatever the orientation of the system with respect to gravity.

One means for ensuring the correct orientation of the cartridge 20 in the cavity 18 of the device has been described with reference to FIGS. 5*a* and 5*b*. The locating portion 25 can be formed as part of the moulded cartridge housing 24 to ensure the correct orientation. However, it will be apparent that other ways of ensuring the correct orientation of the cartridge are possible. In particular, if the housing is injection moulded, there are almost limitless possibilities for the shape of the cartridge. Once the desired internal volume of the cartridge has been chosen, the cartridge shape can be adapted to suit any cavity. FIG. 11*a* is a base view of one possible cartridge housing 70, allowing the cartridge to be oriented in two possible orientations. The cartridge housing 70 includes two symmetrically disposed, grooves 72. The grooves may extend partially or fully up the side of the housing 70. Corresponding ribs (not illustrated) may be formed on the walls of the cavity of the device, so that the cartridge can be received in the cavity in only two possible orientations. In the embodiment of FIG. 11*a* it is possible to have only a single rib in the cavity so that one of the grooves 72 is not filled by a rib and can be used as an air flow channel within the device. It is of course possible to restrict the cartridge to a single orientation within the cavity by providing only a single groove in the housing. This is illustrated in FIG. 11*b*, which shows a cartridge housing 74 with a single groove 76.

Although the embodiments described have cartridges with housings having a substantially circular cross section, it is of course possible to form cartridge housings with other shapes, such as rectangular cross section or triangular cross section. These housing shapes would ensure a desired orientation within the corresponding shaped cavity, to ensure the electrical connection between the device and the cartridge.

The capillary material 22 is advantageously oriented in the housing 24 to convey liquid to the heater assembly 30. When the cartridge is assembled, the heater filaments 36, 37,38 may be in contact with the capillary material 22 and so aerosol-forming substrate can be conveyed directly to the mesh heater. FIG. 12a is a detailed view of the filaments 36 of the heater assembly, showing a meniscus 40 of liquid aerosol-forming substrate between the heater filaments 36. It can be seen that aerosol-forming substrate contacts most of the surface of each filament so that most of the heat generated by the heater assembly passes directly into the aerosol-forming substrate. In contrast, in conventional wick and coil heater assemblies only a small fraction of the heater wire is in contact with the aerosol-forming substrate. FIG. 12b is a detailed view, similar to FIG. 12a, showing an example of a capillary material 27 that extends into the interstices between the filaments 36. The capillary material 27 is the first capillary material shown in FIG. 4. It can be seen that by providing a capillary material comprising fine threads of fibres that extend into the interstices between the filaments 36, transport of liquid to the filaments can be ensured.

In use the heater assembly operates by resistive heating. Current is passed through the filaments 36, 37 38, under the control of control electronics 16, to heat the filaments to within a desired temperature range. The mesh or array of filaments has a significantly higher electrical resistance than the electrical contacts 32 and electrical connectors 19 so that the high temperatures are localised to the filaments. The system may be configured to generate heat by providing electrical current to the heater assembly in response to a user puff or may be configured to generate heat continuously while the device is in an "on" state. Different materials for the filaments may be suitable for different systems. For example, in a continuously heated system, graphite filaments are suitable as they have a relatively low specific heat capacity and are compatible with low current heating. In a puff actuated system, in which heat is generated in short bursts using high current pulses, stainless steel filaments, having a high specific heat capacity may be more suitable.

In a puff actuated system, the device may include a puff sensor configured to detect when a user is drawing air through the mouthpiece portion. The puff sensor (not illustrated) is connected to the control electronics 16 and the control electronics 16 are configured to supply current to the heater assembly 30 only when it is determined that the user is puffing on the device. Any suitable air flow sensor may be used as a puff sensor, such as a microphone.

In a possible embodiment, changes in the resistivity of one or more of the filaments 36, 38 or of the heater element as a whole may be used to detect a change in the temperature of the heater element. This can be used to regulate the power supplied to the heater element to ensure that it remains within a desired temperature range. Sudden changes in temperature may also be used as a means to detect changes in air flow past the heater element resulting from a user puffing on the system. One or more of the filaments may be dedicated temperature sensors and may be formed from a material having a suitable temperature coefficient of resistance for that purpose, such as an iron aluminium alloy, Ni—Cr, platinum, tungsten, or alloy wire.

The air flow through the mouthpiece portion when the system is used is illustrated in FIG. 1*d*. The mouthpiece portion includes internal baffles 17, which are integrally moulded with the external walls of the mouthpiece portion and ensure that, as air is drawn from the inlets 13 to the outlet 15, it flows over the heater assembly 30 on the cartridge where aerosol-forming substrate is being vapourised. As the air passes the heater assembly, vapourised substrate is entrained in the airflow and cools to form an aerosol before exiting the outlet 15. Accordingly, in use, the aerosol-forming substrate passes through the heater assembly by passing through the interstices between the filaments 36, 37, 38 as it is vapourised.

There are a number of possibilities for manufacture and for the materials of the heater assembly. FIG. 13*a* is a schematic illustration of a first method of manufacture of a heater assembly. A roll of polyimide film 80 is provided with an array of apertures 82 in it. The apertures 82 may be formed by stamping. Bands of copper foil 84 are plated onto the polyimide film 80 between the apertures. Ribbons of stainless steel mesh 86 are then clad onto the polyimide film 80 on top of the copper foil 84 and over the apertures 82 in a direction orthogonal to the bands of copper foil. Individual heater assemblies 30 can then be cut or stamped out around each aperture 82. Each heater assembly 30 includes a portion of copper foil on opposite sides of the aperture, forming electrical contacts, and a strip of stainless steel mesh spans the aperture from one portion of copper to the other, as shown in FIG. 6.

FIG. 13*b* illustrates another possible manufacturing process. In the process of FIG. 13*b* a polyimide film 80 of the type used in the process of FIG. 13*a*, is clad with stainless steel foil 90. The polyimide film 80 has an array of apertures 82 formed in it but these apertures are covered by the stainless steel foil 90. The foil 90 is then etched to define filaments 38 spanning the apertures 82 and separate contact portions on opposite sides of the apertures. Individual heater assemblies 92 can then be cut or stamped out around each aperture 82. This provides a heater assembly of the type shown in FIG. 9.

FIG. 13*c* illustrates a further alternative process. In the process of FIG. 13*c* a graphite-based fabric 100 is first prepared. The graphite-based fabric 100 comprises bands of electrically resistive fibres, suitable for use as heater filaments, adjacent bands of relatively non-conductive fibres. These bands of fibres are woven together with bands of relatively electrically conductive fibres that extend perpendicular to the resistive and non-conductive fibres. This fabric 100 is then bonded to a layer of polyimide film 80 of the type described with reference to FIGS. 13*a* and 13*b*, having an array of apertures 82. Individual heater assemblies 102 can then be cut or stamped out around each aperture. Each heater assembly 102 includes a portion of a band of conductive fibres on opposite sides of the aperture and a band of electrically resistive fibres span the aperture.

The cartridge design shown in FIGS. 5*a* and 5*b* has several advantages. However, alternative cartridge designs using the same type of heater assembly are possible. FIG. 14 illustrates an alternative cartridge design that is suited to a different pattern of airflow through the system. In the embodiment shown in FIG. 14, the cartridge 108 is configured to be inserted into the device in the direction indicated by the arrow 110. The cartridge 108 comprises a housing 112 which is shaped like a half cylinder and is open one side. A heater assembly 114 is provided across the open side and is glued or welded to the housing 112. The heater assembly 114 comprises an electrically insulating substrate 116, such as polyimide having an aperture formed in it. A heater element comprising a stainless steel mesh 118 and a pair of contact strips 120 is bonded to the electrically insulating substrate 116 and spans the aperture. The contact strips 120 are bent around the housing 112 to form contact pads on a curved surface of the housing. The electrical contact pads are configured to contact corresponding contacts (not illustrated) in the aerosol-generating device. The housing 112 is filled with a capillary material (not visible in FIG. 14)

soaked in aerosol-forming substrate, as described with reference to the embodiment shown in FIGS. 1a to 1d.

Figure 14:
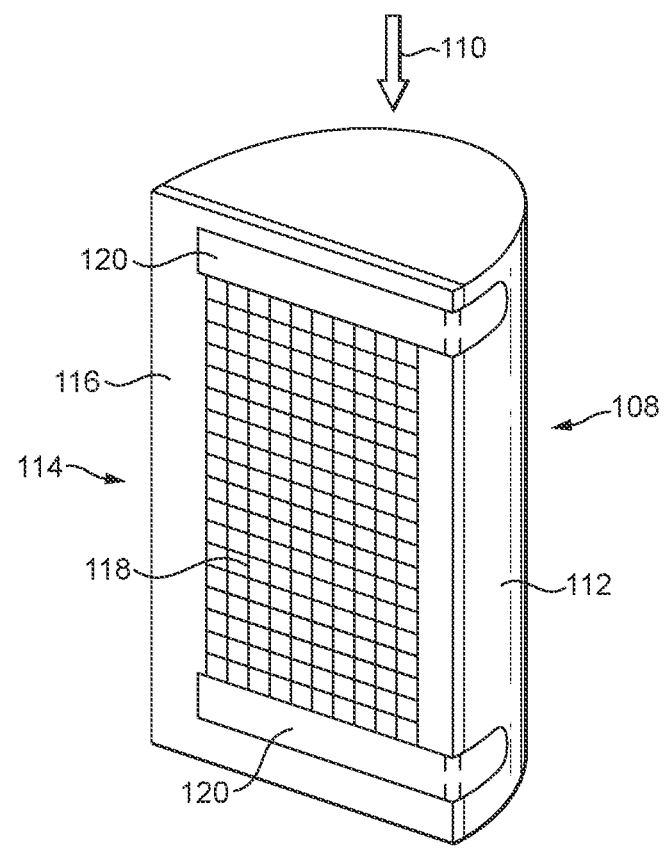
FIG. 14 illustrates an alternative design for a liquid storage portion incorporating a heater assembly.

The cartridge shown in FIG. 14 is configured for airflow past the heater assembly 114 in a direction opposite to arrow 110. Air is drawn into the system through an air inlet provided in a main body of the device and is sucked past the heater assembly 114, into a mouthpiece portion of the device (or cartridge) and into a user's mouth. Air drawn into the system may be directed, for example, in a direction parallel along mesh 118 by appropriate placement of air inlets.

Figure 15A:
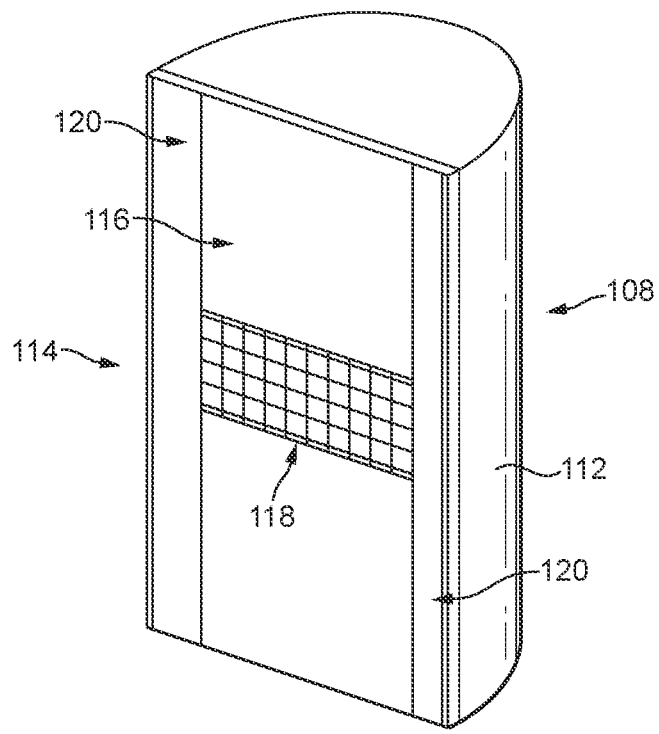
FIGS. 15a and 15b illustrate additional alternative embodiments of a liquid storage portion incorporating a heater assembly.
Figure 15B:
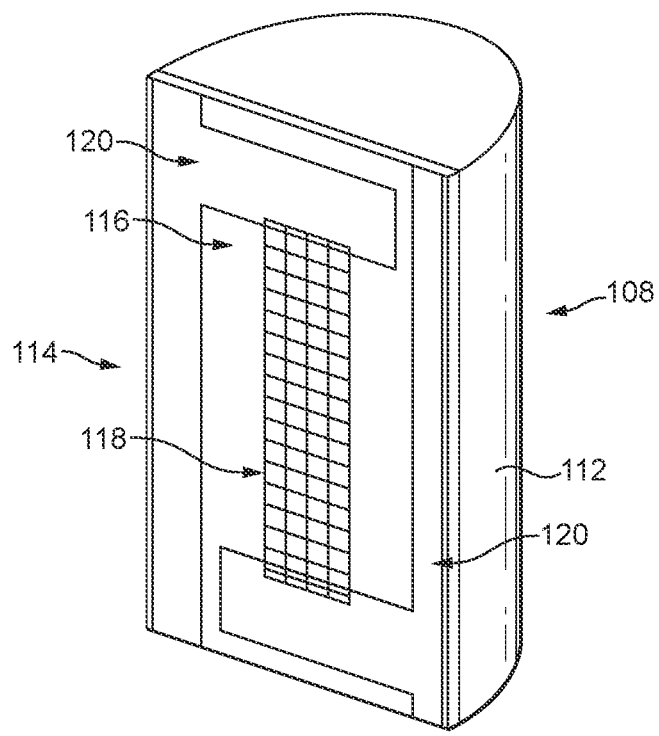

Alternative embodiments of the cartridge 108 are illustrated in FIGS. 15a and 15b. FIG. 15a further includes contract strips 120 spaced apart and running the length of the face having mesh 118. FIG. 15b further includes contacts 120 having roughly an L shape. Both cartridge designs illustrated in FIGS. 15a and 15b may be used to provide even larger contact areas to further ensure easy contact to contacts 19 if required. Strips 120 as illustrated in FIG. 15a may also configured to be slide into a contact 19 that is configured in a rail configuration (not illustrated) for receiving strips 120 to further position the cartridge. Such a rail-type configuration may advantageously provide a periodic cleaning of the contacts 19 as the insertion and removal of the cartridge will have a cleaning effect based on the friction of the contact sliding in and out of the rails.

Figure 16:
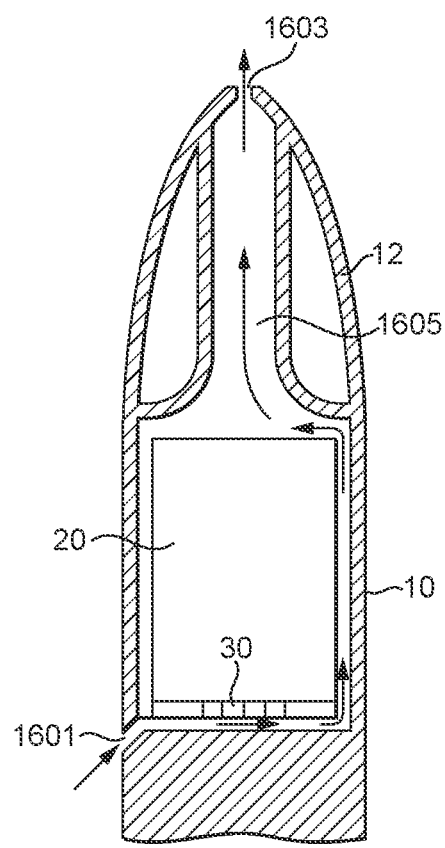
FIG. 16 illustrates an alternative embodiment of the airflow and cartridge orientation with the aerosol-generating device.

FIG. 16 illustrates yet another embodiment of an aerosol-generating system comprising a fluid-permeable electric heater assembly. FIG. 16 illustrates system where the heater assembly 30 is provided at an end of the cartridge 20 that is opposite to the mouthpiece portion 12. Airflow enters an air inlet 1601 and passes by the assembly and through an air outlet 1603 along a flow route 1605. Electrical contacts may be placed in any convenient location. Such a configuration is advantageous as it allows for shorter electrical connections within the system.

Other cartridge designs incorporating a heater assembly in accordance with this disclosure can now be conceived by one of ordinary skill in the art. For example, the cartridge may include a mouthpiece portion, may include more than one heater assembly and may have any desired shape. Furthermore, a heater assembly in accordance with the disclosure may be used in systems of other types to those already described, such as humidifiers, air fresheners, and other aerosol-generating systems.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. An aerosol-generating system comprising a main unit and a cartridge that is removably coupled to the main unit, wherein the cartridge comprises a liquid storage portion containing a liquid aerosol-forming substrate and a fluid-permeable electric heater assembly, and the main unit comprises a power supply, the heater assembly comprising:
   an electrically insulating substrate,
   an aperture being formed in the electrically insulating substrate, and
   a heater element fixed to the electrically insulating substrate, the heater element spanning the aperture and comprising a plurality of electrically conductive filaments connected to first and second electrically conductive contact portions, the first and the second electrically conductive contact portions being disposed on opposite sides of the aperture to one another,
   wherein the first and the second electrically conductive contact portions are configured to allow contact with the power supply, and
   wherein the heater assembly is provided at an end of the cartridge that is opposite to a mouthpiece portion of the aerosol-generating system.

2. The aerosol-generating system according to claim 1, wherein the electrically conductive filaments form interstices, and the electrically conductive filaments are configured to give rise to capillary action in the interstices.

3. The aerosol-generating system according to claim 1, wherein the aerosol-generating system has a longitudinal axis and the heater element is substantially flat and extends perpendicular to the longitudinal axis.

4. The aerosol-generating system according to claim 1, wherein the cartridge comprises the mouthpiece portion.

5. The aerosol-generating system according to claim 1, further comprising an air inlet and an air outlet,
   wherein an airflow route is provided from the air inlet to the air outlet that passes the heater assembly.

6. The aerosol-generating system according to claim 1, wherein the plurality of electrically conductive filaments cover an area of between 10% and 50% of an area of the heater assembly.

7. The aerosol-generating system according to claim 1, wherein an electrical resistance of the electrically conductive filaments is at least two orders of magnitude greater than an electrical resistance of the electrically conductive contact portions.

8. The aerosol-generating system according to claim 1, wherein the heater element has a first face that is fixed to the electrically insulating substrate and the first and the second electrically conductive contact portions are configured to allow contact with an external power supply on a second face of the heater element opposite to the first face.

9. The aerosol-generating system according to claim 1, wherein the electrically conductive filaments lie in a substantially flat plane.

10. The aerosol-generating system according to claim 1, wherein the electrically conductive filaments consist of an array of filaments arranged parallel to one another.

11. The aerosol-generating system according to claim 1, wherein an area of the electrically conductive filaments is less than 25 mm$^2$.

12. The aerosol-generating system according to claim 1, wherein the first and the second electrically conductive contact portions comprise planar contact portions fixed to the electrically conductive filaments.

13. The aerosol-generating system according to claim 1, wherein the heater assembly further comprises at least one filament made from a first material and at least one filament made from a second material different from the first material.

14. The aerosol-generating system according to claim 1, wherein the heater assembly is fixed to a housing of the liquid storage portion.

15. The aerosol-generating system according to claim 1, wherein a housing of the liquid storage portion is rigid and impermeable to fluid.

16. The aerosol-generating system according to claim 1, wherein the aerosol-generating system is an electrically operated smoking system.

\* \* \* \* \*